(12) United States Patent
Mach

(10) Patent No.: US 8,491,649 B2
(45) Date of Patent: Jul. 23, 2013

(54) MEDICAL DEVICE INCLUDING CORRUGATED BRAID AND ASSOCIATED METHOD

(71) Applicant: AGA Medical Corporation, Plymouth, MN (US)

(72) Inventor: Ryan Mach, Durham, NC (US)

(73) Assignee: AGA Medical Corporation, Plymouth, MN (US)

( * ) Notice: Subject to any disclaimer, the term of this patent is extended or adjusted under 35 U.S.C. 154(b) by 0 days.

(21) Appl. No.: 13/709,666

(22) Filed: Dec. 10, 2012

(65) Prior Publication Data

US 2013/0112070 A1    May 9, 2013

Related U.S. Application Data

(62) Division of application No. 12/181,639, filed on Jul. 29, 2008, now abandoned.

(51) Int. Cl.
*A61F 2/06* (2006.01)
*F16L 11/02* (2006.01)
*B21D 15/00* (2006.01)

(52) U.S. Cl.
USPC ............. 623/1.28; 138/121; 72/370.19

(58) Field of Classification Search
USPC ......... 623/1.15, 1.18, 1.2, 1.28, 23.64–23.66, 623/23.7; 138/121–124, 173; 72/180, 302, 72/367.1, 368, 370.06, 370.14, 370.19; 29/17.1, 29/896.6–896.62, 897, 897.31–897.32, 419.1
See application file for complete search history.

(56) References Cited

U.S. PATENT DOCUMENTS

| | | | |
|---|---|---|---|
| 3,105,492 A | 10/1963 | Jeckel | |
| 3,479,670 A | 11/1969 | Medell | |
| 3,577,621 A * | 5/1971 | De Gain | 29/897.2 |
| 3,688,317 A | 9/1972 | Kurtz | |
| 3,908,704 A * | 9/1975 | Clement et al. | 138/121 |
| 3,945,052 A | 3/1976 | Liebig | |
| 4,061,134 A | 12/1977 | Samuels et al. | |
| 4,891,083 A * | 1/1990 | Denoel | 138/173 |
| 6,183,503 B1* | 2/2001 | Hart et al. | 623/1.1 |
| 6,358,275 B1 | 3/2002 | McIlroy et al. | |
| 6,395,021 B1 | 5/2002 | Hart et al. | |
| 6,475,231 B2 | 11/2002 | Dobak, III et al. | |
| 6,773,457 B2 | 8/2004 | Ivancev et al. | |
| 2002/0161394 A1 | 10/2002 | Macoviak et al. | |
| 2005/0033418 A1 | 2/2005 | Banas et al. | |
| 2005/0283186 A1 | 12/2005 | Berrada et al. | |
| 2007/0118207 A1 | 5/2007 | Amplatz et al. | |
| 2007/0168018 A1 | 7/2007 | Amplatz et al. | |
| 2007/0168019 A1 | 7/2007 | Amplatz et al. | |
| 2009/0171386 A1 | 7/2009 | Amplatz et al. | |

* cited by examiner

*Primary Examiner* — Kathleen Holwerda
*Assistant Examiner* — Sarah W Aleman
(74) *Attorney, Agent, or Firm* — Alston & Bird LLP (57) ABSTRACT

Embodiments of the present invention provide medical devices for treating a target site within the body and associated methods for fabricating and delivering medical devices. According to one embodiment, a medical device includes a tubular structure having proximal and distal ends and a side wall extending therebetween. At least a portion of the side wall can have a corrugated surface. The side wall further includes at least one layer of a metallic fabric configured to be compressed and heat set to define the corrugated surface. The tubular structure may comprise an expanded shape, and may be configured to be constrained to a smaller diameter than the expanded shape for delivery within a catheter to a target site and to assume the expanded shape upon release from the catheter.

20 Claims, 9 Drawing Sheets

MEDICAL DEVICE INCLUDING CORRUGATED BRAID AND ASSOCIATED METHOD

CROSS-REFERENCE TO RELATED APPLICATION

The present application is a divisional of U.S. application Ser. No. 12/181,639 filed Jul. 29, 2008, which is herein incorporated by reference in its entirety.

BACKGROUND OF THE INVENTION

1) Field of the Invention

The present invention relates to medical devices and associated methods for treating various target sites within the body and, in particular, to medical devices and associated methods for fabricating and delivering medical devices that respectively include corrugated surfaces.

2) Description of Related Art

Vascular disease is common in the arterial system of humans. This disease often results in a build up of plaque or deposits on the vessel wall, which narrow the vessel carrying oxygenated blood and nutrients throughout the body. If narrowing should occur, for example, in an artery within the heart, blood flow may be restricted to the point of causing pain or ischemia upon body exertion due to the lack of oxygen delivery to the heart muscle. The flow disruption from a severe narrowing of the vessel or a plaque rupture may result in a blood clot formation and flow stoppage which, if occurring in the heart, would result in a heart attack.

Vascular disease may be anywhere in the body, and treating the disease is important to one's health. One method of treatment that is widely adopted is expanding the diseased narrowed sections of a vessel with an angioplasty balloon that is sized to the vessel's healthy diameter. The balloon is inflated to a high pressure to crack and expand the plaque outward, restoring the vessel diameter.

Another technique that may be used to treat the narrowing of a vessel is with a stent. A stent is a thin wall metal tubular member that can be expanded in diameter within the vessel to hold the ballooned segment open after the balloon is removed. Some stents (so-called "balloon-expandable" stents) are placed over a deflated angioplasty balloon and expanded by inflating the balloon, while other types of stents are self-expanding. Both types may be delivered to the treatment site by a catheter in a radially-collapsed configuration and then expanded within the diseased segment of the artery. Both types of stents may be fabricated by laser machining of thin wall metal tubes or may be fabricated from wires formed to a particular shape or by braiding wires into a tubular shape. Balloon-expandable stents are generally made from stainless steel or cobalt-containing alloys, where self-expanding stents tend to be made from highly elastic or pseudo-elastic metals, such as a shape memory nickel-titanium alloy commonly referred to as "Nitinol."

Of particular interest in the design of stents is the amount of radial force that can be achieved for arterial support while minimizing the collapsed deliverable diameter. Stents must also be conformable, when expanded, to the curvature of the target artery segment, and should be flexible in bending in the collapsed deliverable diameter so that the stents can be passed through narrow tortuous arteries to the treatment site. In vessels that are close to the surface of the body, such as in carotid arteries, only self-expanding stents are considered suitable since the stent must spring back from an impact to the body and not close off the artery. Flexibility and good fatigue resistance are important properties for stents placed in arterial segments subject to flexure such as in joints.

Self-expanding tubular stents made of braided filaments of Nitinol wire are very useful due to their high flexibility and ability to be greatly reduced in diameter, by elongation of the braid, for delivery. The braided stents are even more flexible in their reduced diameter state. One limiting aspect of conventional braided Nitinol stents, however, is the ability to achieve high radial support compared to self-expanding stents cut from Nitinol tubing. To achieve greater radial support the braided tube may be fabricated from filaments having a greater diameter, but this increases the collapsed diameter profile and increases deliverable stiffness. An alternative to improve radial support is to heat set the braided stent at the desired expanded diameter with the helix angle of the filaments at a high angle relative to the longitudinal axis of the stent. This increases the length of the collapsed stent and increases the delivery force needed to push the stent through the delivery catheter since the filaments are under greater stress at a given collapsed diameter.

Another application of stents is in stent graft applications. One important application is the treatment of vascular aneurysms, a weakening and thinning of the vessel wall whereby the weakened area causes the vessel diameter to expand outward much like a balloon. The weakened wall is of greater risk of rupture due to pulsing blood pressure. Stent grafts are used to percutaneously reline the aneurysm, sealing against the proximal and distal healthy vessel wall and thus reducing risk of rupture by shielding the weakened wall from carrying the blood pressure. It is important that a seal be achieved on both ends of the graft against the arterial wall and that no leak occurs along the length of the graft. Such leaks would subject the weakened aneurysm wall to blood pressure. To achieve a seal, stent grafts have employed various design means to increase the pressure against the arterial wall at each end, such as incorporating end stents that have greater radial force, using thicker materials near the end, enlarging the expanded diameter of the stent graft at the ends, or adding sealing substances such as filler material. Most of these solutions increase the collapsed profile of the stent graft and increase the stiffness during delivery to the artery.

Another approach to the treatment of aneurysms is the use of a porous tubular stent graft comprised of one or more layers of braided metal. In this approach, the tubular braid is placed directly against the aneurysm before the aneurysm has become dangerous in size. The braid has a maximum expansion diameter matched to the aneurysm maximum diameter and the stent graft incorporates into the wall of the aneurysm by tissue ingrowth, thereby strengthening the wall and inhibiting any further growth of the aneurysm.

Another application of stents or stent grafts is for treating a dissection of a vessel such as, for example, the thoracic aorta, whereby a tear in the vessel lining threatens to cause an aneurysm if not treated. In such cases, the tear may allow blood flow against the adventitial layer of the vessel and must be sealed. A good seal must be achieved between the vessel wall and the stent or stent graft to ensure that blood cannot enter the origin of the dissection. On either side of the origin of the dissection, the stent graft may be more porous as vascular support is the primary attribute for the remainder of the stent graft. A stent graft may achieve the seal by addition of a polymer or textile fabric but this adds to the device delivery profile.

Metallic, "super-elastic," braided, tubular members are known to make excellent vascular occlusion, restrictor, and shunt devices, for implant within the body. These devices are typically braided from filaments of Nitinol and subsequently heat set to "memorize" a final device shape. Such devices may be elongated for delivery through a catheter to a treatment site, and upon removal from the delivery catheter, may self-expand to approximate the "memorized" device heat set shape. The devices have various shapes designed to occlude, restrict flow, or shunt flow to various parts of the vascular anatomy by restricting or diverting blood flow through all or a portion of the device. Since the devices are subjected to blood pressure, there must be sufficient retention force between the device and the vascular wall to prevent device dislodgement.

Therefore, it would be advantageous to provide a medical device having increased radial strength while retaining a small profile and flexibility for delivery to a target site. It would also be advantageous to provide a medical device capable of being sufficiently anchored at a target site and effectively treating the target site.

BRIEF SUMMARY OF THE INVENTION

Embodiments of the present invention provide a medical device, such as, for example, a stent graft, an occluder, a shunt, or a flow restrictor, for treating a target site within the body. For example, one embodiment provides a medical device including a tubular structure having proximal and distal ends and a side wall extending therebetween. At least a portion of the side wall can have a corrugated surface, for example, comprising a plurality of ridges each extending about an entire circumference of the tubular structure. The side wall further includes at least one layer of a metallic fabric, and in some cases a plurality of layers, configured to be compressed and heat set to define the corrugated surface. For example, the metallic fabric can include a shape memory alloy. The ridges of the corrugated surface may extend annularly or helically about the tubular structure. The metallic fabric can additionally be configured to facilitate thrombosis. The tubular structure may comprise an expanded shape, and may be configured to be constrained to a smaller diameter than the expanded shape for delivery within a catheter to a target site and to assume the expanded shape upon release from the catheter. In some cases, the side wall is configured to be elongated such that at least a portion of the corrugated surface has a generally sinusoidal profile along a direction generally aligned with a central axis of the tubular structure.

In some embodiments, the side wall may comprise a plurality of corrugated portions, with each portion having a corrugated surface. At least two corrugated portions may be separated from one another by a non-corrugated portion. One of the corrugated portions can be located adjacent to the proximal end or the distal end.

According to another embodiment, a method for increasing the radial strength or resistance to radial compression of a medical device is provided. The method includes providing a tubular structure comprised of at least one layer of metallic material and having proximal and distal ends and a side wall extending therebetween. In some cases, the side wall can be formed at least partially from a plurality of metallic strands. The tubular structure can be compressed (for example, axially compressed) such that the side wall defines a corrugated surface extending at least partially between the proximal and distal ends. For example, where the side wall includes a plurality of metallic strands, the tubular structure may be compressed until some of the strands buckle to define the corrugated surface. Alternatively, an external or internal mold or both may be used to facilitate formation of the corrugated surface or to induce a thread-like pitch to the corrugation. The compressed tubular structure is then heat set.

In yet another aspect, a method of delivering a medical device, such as that described above, to a target site within the body is provided. The method includes constraining the tubular structure to a smaller diameter (e.g., less than 15 French), for example, by axially elongating the tubular structure. The constrained tubular structure can be positioned in a catheter and delivered, such as, over a guidewire, proximate to the target site. The tubular structure can then be deployed from the catheter such that the tubular structure assumes the expanded shape, either by self-expanding into the expanded shape or by being compressed and thereby urged back towards the expanded shape.

According to one embodiment, a medical device for treating a target site within the body is provided. The medical device includes a tubular structure, such as, for example, a stent graft, a shunt, a flow restrictor, or an occluder, having proximal and distal ends and a side wall extending therebetween. At least a portion of the side wall can be a corrugated portion that extends partially between the proximal and distal ends. The corrugated portion has a first diameter and has a corrugated surface. The side wall further includes at least one non-corrugated portion adjacent the corrugated portion. The non-corrugated portion may extend partially between the proximal and distal ends, and has a second diameter not equal to (e.g., less than) the first diameter. The side wall may include at least one layer of a metallic material configured to be compressed and heat set to define the corrugated portion. The at least one corrugated portion can be located adjacent to the proximal end or the distal end. In some embodiments, the side wall may include a plurality of corrugated portions, with a pair of the corrugated portions separated by the at least one non-corrugated portion.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site within the body, such as excluding or occluding various vascular abnormalities, which may include, for example, excluding an aneurysm, or occluding an Arterial Venous Malformation (AVM), an Atrial Septal Defect (ASD), a Ventricular Septal Defect (VSD), a Patent Ductus Arteriosus (PDA), a Patent Foramen Ovale (PFO), a Left Atrial Appendage (LAA), conditions that result from previous medical procedures such as Para-Valvular Leaks (PVL) following surgical valve repair or replacement, and the like. The device may also be used as a flow restrictor or a shunt, filter or other type of device for placement in the vascular system, as well as a graft for lining a lumen of a vessel. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a lesion, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, or the like.

As used herein the term "proximal" shall mean closest to the operator (less into the body) and "distal" shall mean furthest from the operator (further into the body). In positioning of the medical device from a downstream access point, distal is more upstream and proximal is more downstream.

As explained in further detail below, embodiments of the present invention provide medical devices for treating various target sites. The medical devices may include one or more corrugated surfaces that may increase the radial strength of the devices such as by having an increased density. Thus, the corrugated surfaces may improve the fixation of the medical devices at a target site. Moreover, the corrugated surfaces may facilitate occlusion at the target site for treating various abnormalities, while remaining conformable and flexible for delivery to various target sites.

Figure 1:
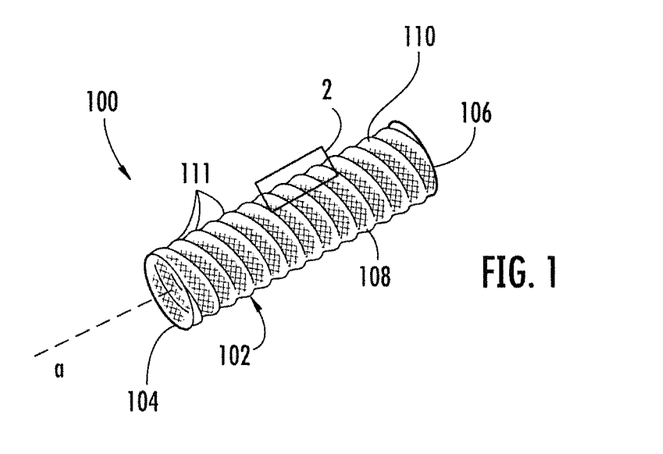
FIG. 1 is a perspective view of a stent graft configured in accordance with an exemplary embodiment.

With reference to FIG. 1, therein is shown a perspective view of a medical device 100 for treating a target site within a body. The medical device 100 of FIG. 1 could be used in a variety of ways, including as a stent, a stent graft, an occluder, a shunt, or a flow restrictor, depending on the application. As a matter of convenience, the medical device 100 will simply be referred to as a stent graft. The stent graft 100 includes a structure, such as a tube 102, having proximal and distal ends 104, 106 and a side wall 108 extending therebetween. The side wall 108 may be cylindrical in shape or any other suitable shape for being positioned within a vessel or the like. The side wall 108 has a corrugated surface 110 that includes a plurality of corrugations 111.

Figure 2:
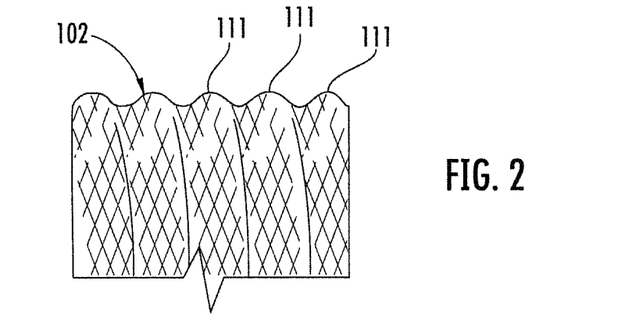
FIG. 2 is a magnified side elevational view of the area labeled 2 in FIG. 1.

Referring to FIG. 2, therein is shown a magnified view of the stent graft 100 that more clearly illustrates the tube 102 and corrugated surface 110. The tube 102 can include at least one layer (and in some cases multiple layers) of an occlusive material, such as a metallic fabric 112. The fabric 112 can be composed of multiple metallic strands 114. Although the term "strand" is discussed herein, "strand" is not meant to be limiting, as it is understood the fabric may comprise one or more wires, cords, fibers, yarns, filaments, cables, threads, or the like, such that such terms may be used interchangeably. The stent graft 100 may be a variety of occlusive materials capable of at least partially inhibiting blood flow therethrough in order to facilitate the formation of thrombus and epithelialization around the device.

According to one embodiment, the metallic fabric may include two sets of essentially parallel generally helical strands, with the strands of one set having a "hand", i.e., a direction of rotation, opposite that of the other set. The strands may be braided, interwoven, or otherwise combined to define a generally tubular fabric. The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

For example, in one embodiment, the fabric 112 may form a braided tubular member by wrapping a number of filaments in a left helix about a mandrel (e.g., a 15 mm diameter mandrel), while other filaments are wrapped in a right helix. The filaments of one helical direction alternately pass over and then under the filaments of the other helical direction (e.g., two at a time) to form the braided tubular member. The filaments can be, say, wire filaments with diameters of about 0.0035 inches, and can be spaced apart in parallel fashion with 36 filaments in each helical direction and a pick count of 50. Commercial braiding machines, such as those offered by Wilhelm STEEGER GmbH & Co. (Wuppertal, Germany) can be utilized to perform such a braiding process. Following braiding, the braided tubular member may be placed in an oven until reaching a temperature of about 425° C. for about 15-20 seconds in order to stabilize the diameter of the braided tubular member and to improve handling by minimizing unraveling.

The metallic fabric 112 can be configured to be compressed and heat set to define the corrugated surface 110. That is, the fabric 112 can be composed of materials and/or structurally arranged such that compression causes the fabric to assume a corrugated configuration at a surface of the fabric. The constituent materials can further be configured such that heat can then be applied to the fabric 112 in order to allow the fabric to maintain the corrugated configuration, under at least some conditions, without the application of external force. The process by which a medical device incorporating a corrugated metal fabric can be produced is discussed in more detail below. In one embodiment, metallic fabric 112 can include a shape memory alloy, such as Nitinol (e.g., 72 strands of Nitinol wire). It is also understood that the stent graft 100 may comprise various materials other than Nitinol that have elastic properties, such as spring stainless steel, trade named alloys such as Elgiloy, Hastalloy, Phynox, MP35N, or CoCrMo alloys.

The metallic fabric 112 can also be configured to facilitate thrombosis, for example, by at least partially inhibiting blood flow therethrough in order to facilitate the formation of thrombus and epithelialization around the stent graft 100. In particular, the braid of the metallic fabric 112 may be chosen to have a predetermined pick and pitch to define openings or fenestrations so as to vary the impedance of blood flow therethrough. For instance, the formation of thrombus may result from substantially precluding or impeding flow, or functionally, that blood flow may occur for a short time, e.g., about 3-60 minutes through the metallic fabric 112, but that the body's clotting mechanism or protein or other body deposits on the braided wire strands results in occlusion or flow stoppage after this initial time period. For instance, occlusion may be clinically represented by injecting a contrast media into the upstream lumen of the stent graft 100 and if no contrast media flows through the wall of the stent graft after a predetermined period of time as viewed by fluoroscopy, then the position and occlusion of the stent graft is adequate. Moreover, occlusion of the target site could be assessed using various ultrasound echo doppler modalities.

Figure 3:
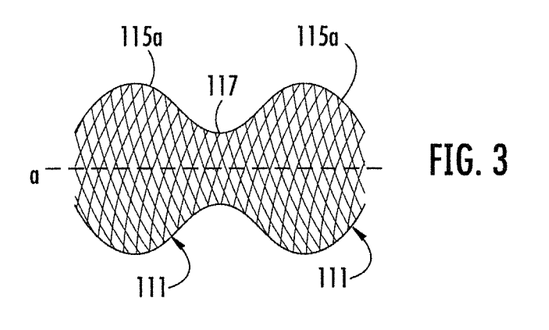
FIGS. 3 and 4 are schematic side views of stent grafts configured in accordance with exemplary embodiments, the stent grafts respectively demonstrating differing arrangements of the corrugations of the corrugated surface.
Figure 4:
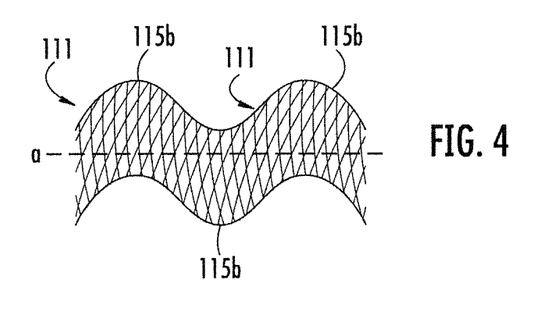
Figure 5:
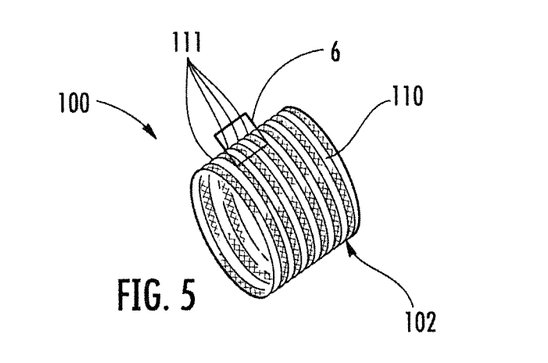
FIG. 5 is a perspective view of the stent graft of FIG. 1 showing the stent graft in an axially compressed configuration relative to the configuration of FIG. 1.

Referring to FIGS. 2-4, the corrugated surface 110 may include a plurality of corrugations 111. The corrugations 111 may include a plurality of annular ridges 115a that each extend about an entire circumference of the tube 102 and that are separated from one another by grooves 117 (e.g., peaks and valleys). Alternatively, or in some cases additionally, the tube 102 may include adjacent staggered portions 115b that are transversely offset from one another along the length of the tube 102, with respect to a central axis a defined by the tube, such that the staggered structure of the tube collectively define the corrugations 111. In either case, the corrugated surface 110 may have a somewhat sinusoidal profile along a direction aligned with the central axis a. Note that the portions constituting peaks on one surface become valleys when traveling circumferentially around to the other side. The ridges of the corrugated surface extend circumferentially about the tube at various angles.

Figure 6:
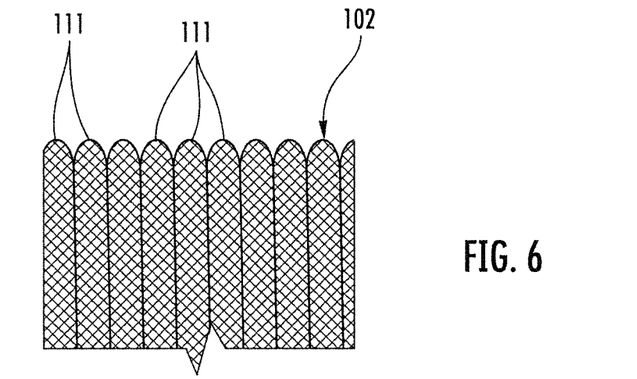
FIG. 6 is a magnified side elevational view of the area labeled 6 in FIG. 5.
Figure 7:
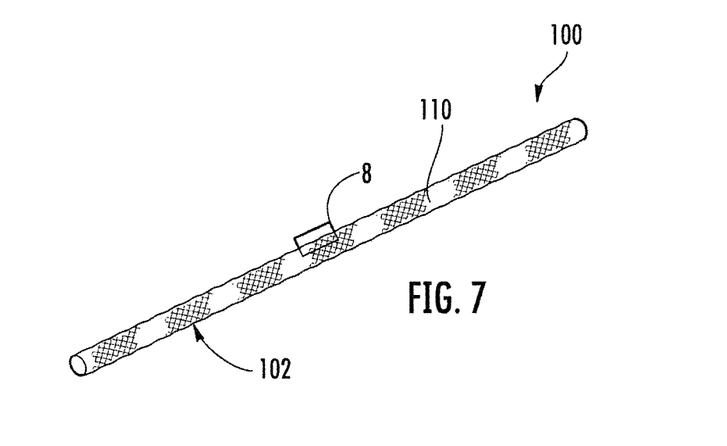
FIG. 7 is a perspective view of the stent graft of FIG. 1 showing the stent graft in an axially elongated configuration relative to the configuration of FIG. 1.
Figure 8:
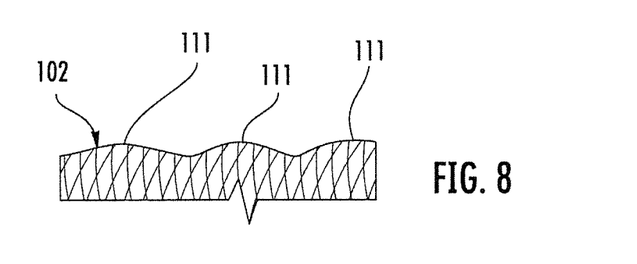
FIG. 8 is a magnified side elevational view of the area labeled 8 in FIG. 7.

Referring to FIGS. 1, 2, and 5-8, the tube 102 may have an "expanded" shape (e.g., as depicted in FIG. 3), and the tube may be configured to be constrained so as to have a smaller diameter than in the expanded shape. The shape of the tube 102, when constrained, can be referred to as the "reduced" shape, and an example of a reduced shape is depicted in FIG. 7. In some embodiments, the tube 102 can be forced into the reduced shape, and will assume the expanded shape upon the removal of any constraining forces. As will be discussed further below, the reduced shape may facilitate delivery of the medical device 100 within a catheter to a target site, at which point the medical device can be released from the catheter in order to allow the tube 102 to assume the expanded shape.

In embodiments in which the tube 102 includes metal fabric 112 that is braided, the braided structure may allow for the tube to be forced into the reduced shape by axially elongating the tube. For example, the tube 102 could be axially elongated by applying axially-directed tension to the tube, or by radially compressing the tube. As the tube 102 is elongated, at least a portion of the corrugated surface 110 may have a generally sinusoidal profile along a direction generally aligned with a central axis a. Considering the embodiment described above in which a braided tubular member is formed by wrapping 72 Nitinol strands with diameters of about 0.0035 inches in left and right helices about a 15 mm mandrel, the filaments being spaced apart in parallel fashion with 36 filaments in each helical direction and having a pick count of 50, axial elongation of a braided member having a length of about 4 cm in the corrugated configuration (resulting in an inside diameter of about 16 mm and an outside diameter of about 17-18 mm) results in a reduced shape in which the braided member is about 70 cm long (or an elongation ratio of about 17.5:1) and a collapsed diameter of less than about 3 mm (9 French) or even 2 mm (6 French). As such, a ratio of the inner diameters of the tube 102 for the expanded configuration and the reduced configuration may be about 8:1.

Figure 9:
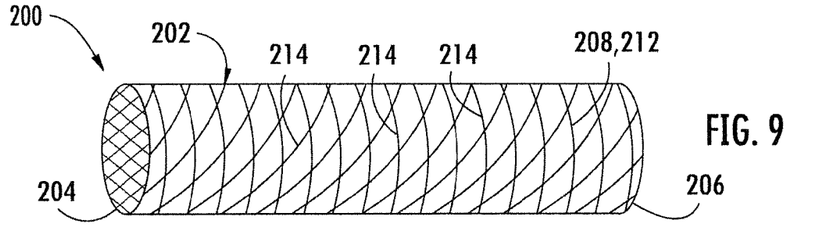
FIGS. 9-13 are perspective views of a stent graft at various stages of a process for producing a stent graft configured in accordance with an exemplary embodiment.

Referring to FIGS. 9-13, therein are schematically depicted various aspects of a process for producing a medical device as discussed above, or, relatedly, for increasing the radial strength of a medical device by effecting a structure as discussed above. As shown in FIG. 9, the process includes forming a structure in a non-compressed configuration, such as a tube 202, that includes at least one layer 212 (and in some cases multiple layers) of metallic material, the tube having proximal and distal ends 204, 206 and a side wall 208 extending therebetween. In the illustrated embodiment, the side wall 208 is formed by the layer 212 of metallic material and is entirely cylindrical. In other embodiments, the side wall need not be entirely cylindrical, although at least a portion of the side wall would usually be cylindrical in shape in order to conform to a vessel lumen.

It is noted that, in some embodiments, a traditional stent/stent graft structure can be used as the tube 202. For further details regarding the structure, exemplary dimensions, and methods of making a stent/stent graft, Applicants hereby incorporate by reference U.S. Patent Appl. Publ. No. 2007/0168018, filed on Jan. 13, 2006, and U.S. Patent Appl. Publ. No. 2007/0168019, filed on Jan. 17, 2007, herein in their entirety.

Figure 10:
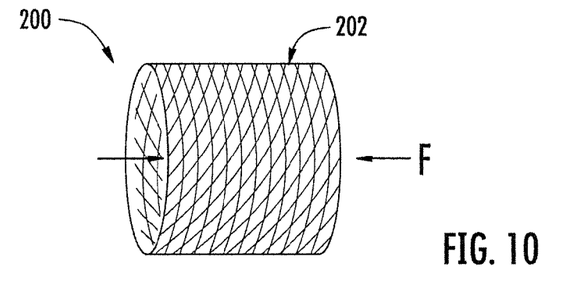
Figure 11:
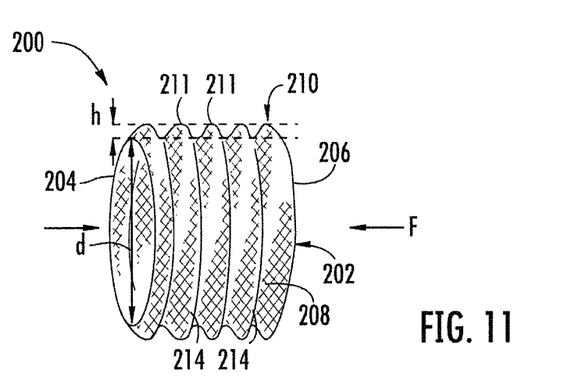
Figure 12:
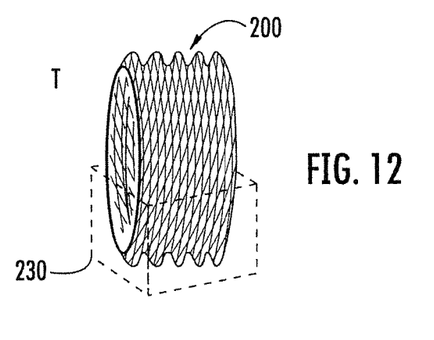
Figure 13:
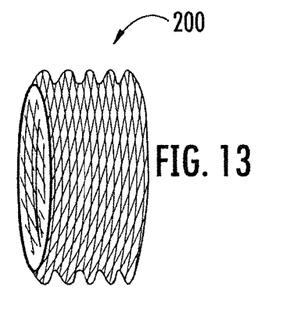

Referring to FIGS. 10 and 11, the cylindrical portion of the side wall 208 (which in the illustrated case is the entire side wall) can be compressed such that the sidewall defines a corrugated surface 210 extending at least partially (or, in the illustrated case, completely) between the proximal and distal ends 204, 206. For example, the side wall 208 can be axially compressed, as depicted in FIG. 11. In some embodiments, the tube 202 can be at least partially formed from a plurality of metallic strands 214. The tube 202 may be compressed in order to cause the strands 214 to be condensed into a somewhat closely-packed (or even abutting) configuration, as shown in FIG. 10 (the "compressed, non-corrugated configuration"). The tube 202 may then be further compressed in order to cause some of the strands 214 to buckle, usually repeatedly, as shown in FIG. 11 (the "corrugated configuration"). The repeatedly buckled configuration of the strands 214 may then define the corrugated surface 210.

In some embodiments, the tube 202 may be formed from 72 Nitinol wires of about 0.002 inches in diameter and have a braid pick count of about 48 ppi prior to compression. The tube 202 may have an outer diameter of about 15.621 mm and an inner diameter of about 15.392 mm (i.e., a nominal diameter of about 15.5 mm). Thus, each corrugation 211 may have a wall thickness of about 0.20-0.23 mm (0.008 to 0.009 inches). In addition, the corrugated surface 210 may have corrugations 211 spaced apart from one another by about 0.25 mm (0.010 inches).

As mentioned above and shown in FIG. 11, the heights h of the corrugations 211 may be small relative to the diameter d of the tube 202. However, for some embodiments, the length of the tube 202 in the corrugated configuration can be as little as 25% of the length of the tube when in the compressed, non-corrugated configuration. As such, in cases where the embodiments include metal fabric composed of a plurality of strands, the strand density in the corrugated configuration is significantly increased with respect to the non-compressed or compressed, non-corrugated configuration. Also, some embodiments may exhibit a circumferential stiffness or "hoop strength" per unit length of the tube 202 when in the corrugated configuration that is markedly increased relative to the hoop strength per unit length of the tube when in the non-compressed or compressed, non-corrugated configuration. This increase in strength in the corrugated configuration may be especially pronounced for embodiments incorporating braided metal fabric, as the corrugated configuration may result in a higher helix angle and a higher density of the constituent metal strands. Thus, the corrugated surface may provide an increase in radial strength or resistance to radial compression.

Once the side wall 208 has been compressed, heat can be applied to the tube 202 in order to heat set the side wall 208. In some cases, compressive forces may continue to be applied to the side wall 208 simultaneously with heat, for example, by placing the medical device 200 into a mold 230 (see FIG. 12). The device 200 and mold 230 can then be together placed into an oven and heated. In other cases, the side wall 202 may be compressed and then all compressive forces may be removed before heat is applied. In either case, following heat setting of the side wall 208, the side wall will exhibit a persistent corrugated surface 210 without the application of a compressive or restrictive force (see FIG. 13). As mentioned previously, the corrugated surface may have helical ridges that provide a lead or thread-like pitch. The corrugated surface may be formed, for example, using an external or internal mold or both to facilitate formation of the corrugated surface or to induce a thread-like pitch to the corrugation.

The device 200 can be heated until the side wall 208 reaches the desired temperature, which temperature is dictated by the materials used to form the side wall and is the temperature at which the side wall will become heat set. For example, for side walls composed of a shape memory alloy, the "desired" temperature would be the temperature at which formation of the material's austenitic phase is complete. In some embodiments, side walls formed of 72 Nitinol strands may be sufficiently heat set by heating the device 200 from room temperature to about 520° C. over a span of about 18 minutes.

Figure 25:
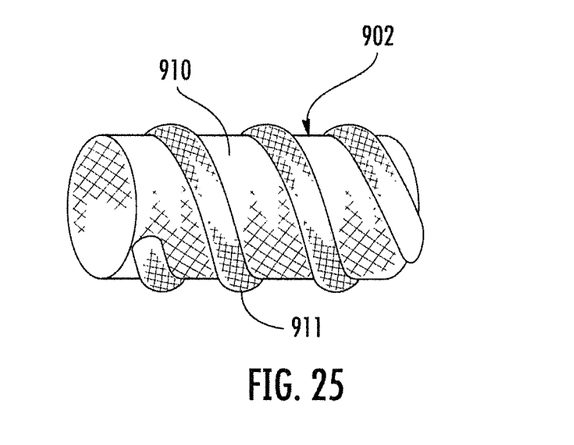
FIG. 25 is a perspective view of a stent graft according to another embodiment of the present invention.

The particular configuration of the corrugated surface may depend on the wire diameter, number of wires, type of corrugations, and braided tube diameter. For example, the corrugated surface may include a plurality of annular ridges, or according to one exemplary embodiment shown in FIG. 25, the corrugated surface 910 of the braided tube 902 may include one or more spiral or helical ridges 911 that extend both circumferentially and longitudinally along the tube. The corrugations 911 may have a lead or thread-like pitch. For instance, the corrugated surface 910 may match that of a 5-10×11 threads/inch bolt. Thus, the corrugated surface 910 may have 11 corrugations per inch. The tube 902 may be formed using 144 Nitinol wires of about 0.003 inches in diameter that are formed on a 22 mm diameter mandrel and heat set at about 530° C. over 10 minutes. The tube 902 may have a braid pick count of about 75 ppi. In its relaxed and expanded configuration, the inner diameter of each corrugation 911 may be about 16 mm, while the outer diameter may be about 19.2 mm.

Figure 26:
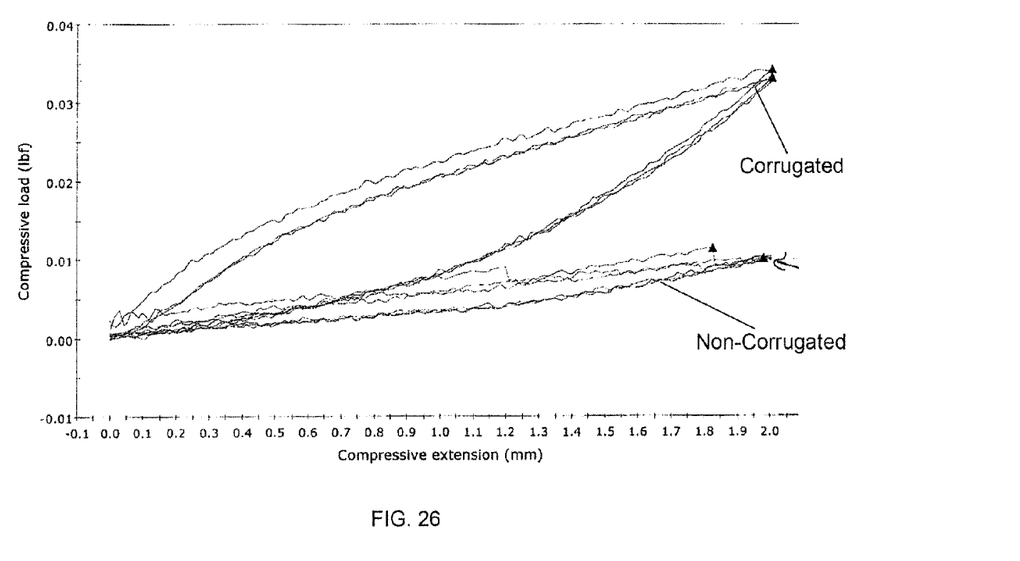
FIGS. 26 and 27 illustrate graphical representations of experimental data for various stent grafts according to embodiments of the present invention.
Figure 27:
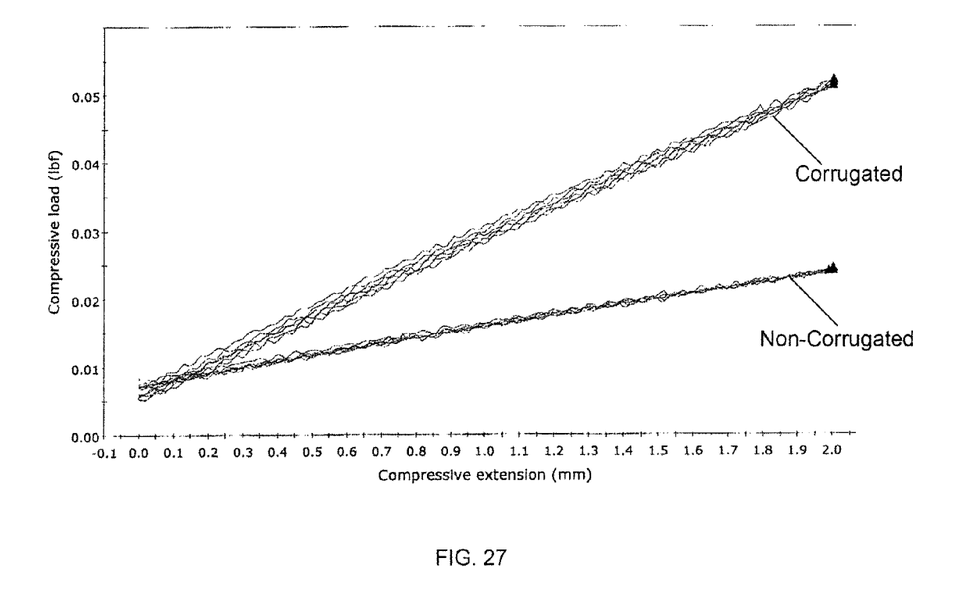

FIGS. 26 and 27 illustrate exemplary data showing the increased radial strength or resistance to radial compression that may be experienced with embodiments of the present invention. In particular, FIG. 26 shows compressive extension (mm) plotted against compressive load (lbf) for a medical device having a corrugated surface, such as that shown in FIG. 25, and for a medical device not having corrugations. The medical device without corrugations was braided in the same manner as the corrugated medical device. The test involved radially compressing each medical device between 1 inch square plates 2 mm and then releasing the force. FIG. 26 shows that the medical device having the threaded corrugations has larger radial strength than the medical device without corrugations. For instance, at the maximum extension of 2 mm, the threaded device has a resistive compressive load of about 0.033 lbf, while the medical device without corrugations exhibits a resistive compressive load of about 0.01 lbf. Therefore, the medical device with threaded corrugations may provide at least a three-fold increase in resistance to radial compression.

FIG. 27 depicts a similar graph for the corrugated medical device, such as a medical device shown in FIG. 6 that includes a corrugated surface formed by axial compression, and for a non-corrugated medical device, wherein the non-corrugated medical device has been braided in a similar manner. The corrugated medical device again exhibits a greater radial strength than the non-corrugated medical device. In particular, at 2 mm of compressive extension, the corrugated medical device provides a resistive compressive load of 0.051 lbf while the non-corrugated medical device has a resistive compressive load of about 0.025 lbf. Thus, in this particular example, the corrugated medical device provides about 2 times the resistance to radial compression.

Figure 14:
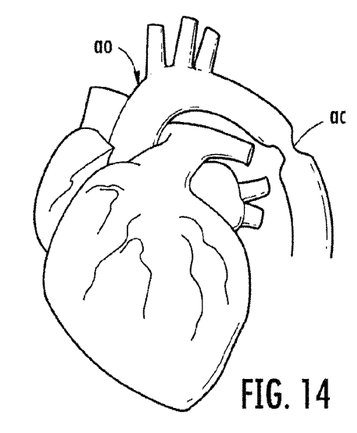
FIGS. 14 and 15 are sketches of an aortic coarctation (14) and a stent graft placed in the coarctation (15) according to one embodiment of the present invention.
Figure 15:
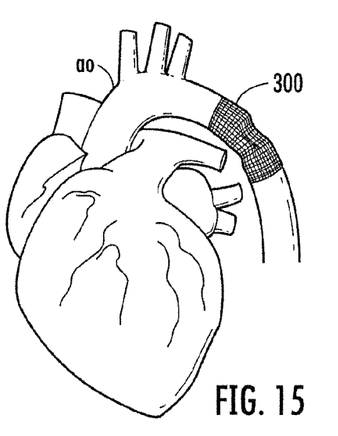

As mentioned earlier, medical devices configured in accordance with exemplary embodiments can be useful in a variety of medicinal purposes. Referring to FIGS. 14 and 15, therein are depicted the use of a stent graft 300 configured in accordance with an exemplary embodiment for treating a vascular abnormality, an aortic coarctation ac, at a target site within a body, e.g., the lumen of an aorta ao. Aortic coarctation is a narrowing of the aorta in the area where the ductus arteriosus inserts. In the illustrated embodiment, the stent graft 300 has a corrugated surface along its entire length. By delivering the stent graft 300 to the location of the aortic coarctation ac, the stent graft tends to urge wider the affected portion of the aorta ao. The corrugated configuration of the stent 300 increases the circumferential stiffness of the stent graft, thereby enhancing the ability of the stent graft to urge open the affected vessel and to maintain the patency of the vessel.

Referring to FIGS. 1, 7, 16, and 17, in order to deliver the stent graft 100 to a target site within the body, the tube 102 may be first constrained from an expanded shape (see FIG. 1) to a smaller diameter (see FIG. 7). For example, where the metallic material 112 of the tube 102 is a braided metallic fabric that forms a braided tubular member, the tube may have a first diameter and may be capable of being collapsed to a second, smaller diameter by axially elongating the ends of the tube. In some embodiments, the tube 102 may be constrained to an outer diameter of less than 15 French for delivery within a catheter.

The constrained tube 102 can then be positioned in a delivery catheter 440 (see FIG. 16), which is a catheter that defines an axial bore 441 (FIG. 17) for receiving the tube therein. The tube 102 may be coupled to a delivery device 444. According to one embodiment, the delivery device 444 includes an elongated tubular member 445 having an inside diameter sized to receive a guidewire 442 or, alternatively, the delivery device may employ a solid wire or cable in place of the tubular member (discussed further below). The tubular member 445 may, for example, be fabricated from a high density polyethylene, Pebax nylon, polyimide, hollow cable, composite braided polymer, or even a hypotube of stainless steel or Nitinol. The tubular member 445 may pass within the delivery catheter 440 (i.e., through the bore 441) and, in one embodiment, includes a molded distal end 446 that has an outside profile matching the interior contour of the constrained tube 102.

Figure 16:
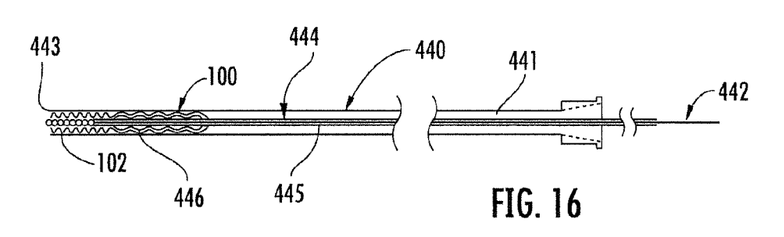
FIGS. 16 and 17 are side elevational views of a system for delivering a stent graft to a target site in a body according to one embodiment of the present invention.
Figure 17:
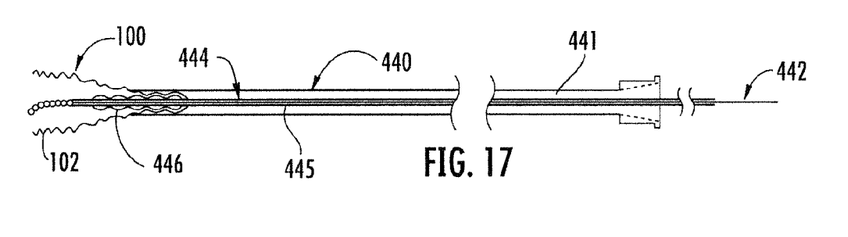

The delivery device 444 may extend through the bore 441 of the delivery catheter 440 such that the molded distal end 446 of the delivery device extends beyond the distal end 443 of the catheter. The tube 102 can be coupled to the molded distal end 446 of the delivery device 444, and thereafter, pulling the delivery device 444 proximally relative to the delivery catheter 440 moves the tube into the delivery catheter 440. The tube 102 is then trapped between the delivery catheter 440 and the molded distal end 446 of the delivery device 444 in order to maintain the tube in the constrained configuration during delivery.

The catheter 440 and stent graft 100 can be advanced over the guidewire 442 until disposed at the target site, where the tube 102 can be deployed from the catheter by advancing the delivery device 444 distally relative to the catheter. Alternatively, the catheter may be retracted proximally relative to the delivery device a small distance followed by advancement of the delivery device relative to the catheter. Once the tube 102 has been advanced completely out of the catheter 440, the tube may assume the expanded shape (to the extent permitted by the surrounding vasculature). In some embodiments, the tube 102 may self-expand upon being deployed from the catheter 440 as the constraining forces of the catheter are removed. In other embodiments, the tube 102 may be physically urged into or toward the expanded shape, say, by inflating a balloon located within the tube (post dilatation), or by axially compressing the tube using the delivery device 444 during deployment from the catheter 440 but prior to release of the proximal end of the tube. In any event, until such time as the tube 102 has been advanced entirely beyond the catheter 440, the stent graft 100 may be fully retrievable by the catheter for removal or repositioning.

In some embodiments, medical devices configured in accordance with exemplary embodiments may include multiple corrugated portions. For example, referring to FIG. 18, a medical device, such as a stent graft 500, a shunt, a flow restrictor, or an occluder, may have a structure, such as a tube 502, having proximal and distal ends 504, 506 and a side wall 508 extending therebetween. The side wall 508 has at least a portion that is cylindrical in shape and includes at least one corrugated portion 509a that extends partially between the proximal and distal ends 504, 506. The corrugated portion 509a has a first diameter d1 and has a corrugated surface 510 including a series of corrugations 511. The side wall 508 can further include at least one non-corrugated portion 509b adjacent the corrugated portion 509a. The non-corrugated portion 509b also extends partially between the proximal and distal ends 504, 506, and has a second diameter d2 that is not equal to (e.g., less than) the first diameter d1.

The tube 502 may include at least one layer 512 (and in some cases multiple layers) of a metallic material that is configured to be compressed and heat set to define the corrugated portion 509a. The metallic material may be configured to facilitate thrombosis. The corrugated portion 509a and non-corrugated potion 509b can be arranged such that the corrugated portion is adjacent to the proximal end 504 (as shown in FIG. 18) or to the distal end 506, or such that the non-corrugated portion is located centrally in the tube 502 and adjacent to neither end.

In order to fabricate a medical device such as the stent graft 500, one can start with a stent graft including an uncompressed tube as discussed above (see the stent graft of FIG. 9, which could be used to produce the stent graft 500 above). However, when forming the tube 502 of the stent graft 500 in order to define the corrugated portion 509(a), it may not be necessary to compress the tube along its entire length but, instead, only a section corresponding to the corrugated portion 509a is axially compressed. This allows, for example, for a stent graft 500 to have one or more compressed corrugated portions 509a while the remaining portion(s) of the stent graft has non-corrugated portion(s). Such targeted axial compression can be applied to any region(s) of the tube 502. Thus, a wide array of medical devices may be fabricated with one or more corrugated portions that may have increased material density or improved hoop strength relative to the non-corrugated portions.

Figure 18:
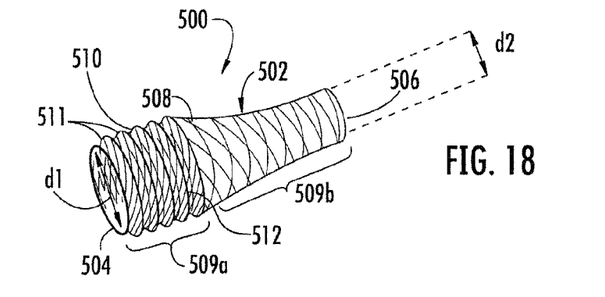
FIG. 18 is a perspective view of a stent graft having both corrugated and non-corrugated portions according to one embodiment of the present invention.
Figure 19:
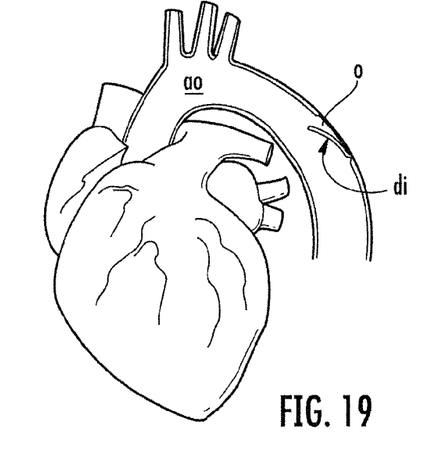
FIGS. 19 and 20 are side elevational views demonstrating the use of a stent graft configured in accordance with an exemplary embodiment in treating an aortic dissection.
Figure 20:
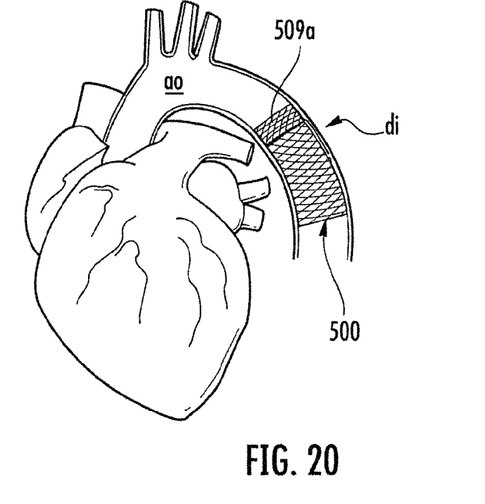

Referring to FIGS. 18-20, the stent graft 500 may prove useful in the treatment of a dissection di of the aorta ao. It is desirable to seal the origin o of the dissection as well as add support to the vessel for healing, thereby keeping the vessel fully open. With these objectives in mind, the stent graft 500 is deployed in the aorta ao so as to support the vessel wall in the area of the dissection di and further such that the corrugated portion 509a is adjacent to the area of the vessel wall corresponding to the origin o of the dissection. In this way, the stent graft 500 provides general support for the vessel while providing added pressure to the area of the vessel wall corresponding to the origin o of the dissection, wherein the additional pressure is due to the increased circumferential stiffness of the stent graft in the corrugated portion 509a.

Figure 21:
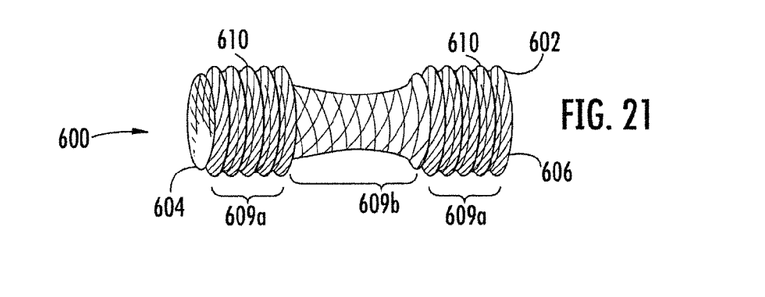
FIGS. 21 and 22 are side elevational views of stents having multiple corrugated portions separated by non-corrugated portions according to exemplary embodiments of the present invention.
Figure 22:
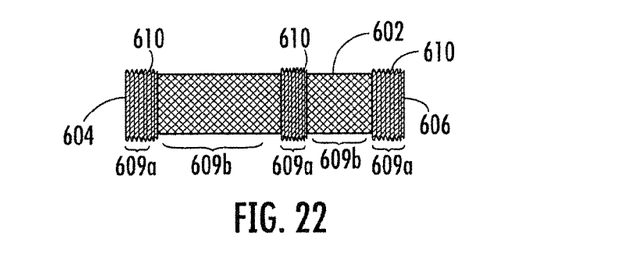
Figure 23:
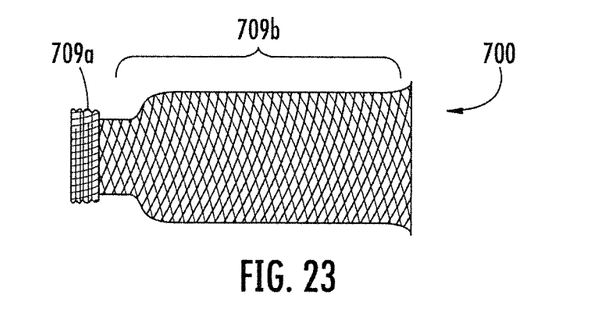
FIG. 23 is a side elevational view of a stent graft configured in accordance with another exemplary embodiment.

Referring to FIGS. 21 and 22 and according to additional embodiments, each medical device 600 may include a tube 602 with a plurality of corrugated portions 609a that each has a corrugated surface 610. Some or all of the corrugated portions 609a can be respectively separated from one another by non-corrugated portions 609b. In some embodiments, corrugated portions 609a may be located adjacent to the proximal end 604 of the tube 602, the distal end 606, or both. Overall, the methods described herein can be used to create medical devices with a wide range of geometries that may be tailored for target applications. For example, referring further to FIG. 23, in still another embodiment, a stent graft 700 can be developed with a corrugated portion 709a and a non-corrugated portion 709b that increases in diameter when moving away from the corrugated portion. This stent graft 700 may be well suited for treating of abdominal aortic aneurysms, such as by providing opposed ends configured to anchor the stent graft on either side of the aneurysm.

An exemplary procedure for delivering a stent graft configured in accordance with an exemplary embodiment, including the above discussed embodiments, to a target location within the thoracic aorta is now described. First, access to the femoral artery is gained, for example, by use of the Seldinger technique, and an introducer sheath is placed through the skin into the femoral artery. A guidewire is advanced through the femoral and iliac arteries and along the upper aorta until the point at which it crosses the target location. The stent graft is then loaded into the bore of a delivery catheter using a delivery device. The delivery device includes a distal tubular member with a bead at the distal end attached to an axial manipulation wire, cable or tube that engages the proximal end of the stent graft between the tubular member and bead, such as disclosed in patent application U.S. Patent Appl. Publ. No. 2007/0118207, which is incorporated in its entirety herein. The delivery device is then retracted proximally through the delivery catheter until the stent graft just extends out of the distal end of the delivery catheter. It is noted that an introducer tool may prove helpful in accomplishing this step.

The proximal end of the guidewire may be inserted into the distal end of the stent graft, delivery device, and the delivery catheter, and the delivery catheter may be advanced partially over the guidewire. While the distal end of the delivery catheter is still outside the body, the delivery device is pulled proximally to draw the distal end of the stent graft fully into the delivery catheter. The delivery catheter can then be introduced through the access sheath and over the guidewire to the target site within the body.

When the delivery catheter reaches the target site in the body, the delivery device can be advanced to expel the distal end of the stent graft from the delivery catheter or alternatively the delivery catheter can be pulled proximally relative to the delivery device. Prior to extending the contoured portion of the delivery device out the distal end of the delivery catheter, the position of the stent graft may be assessed. The location of contact between the stent graft and the vessel wall can be observed with various imaging techniques, such as angiography in order to assure appropriate placement of the stent graft. If the stent graft is not placed correctly, it can be drawn back into the catheter by pulling proximally on the delivery device while holding the delivery catheter stationary. If the placement is as intended, the distal portion of the delivery device may be extended out of the distal end of the delivery catheter and the beaded portion advanced distally relative to the tubular member to release the stent graft. The delivery catheter, delivery device, and guidewire can then be removed from the body.

In an alternative procedure for delivering a stent graft to a target location in accordance with an exemplary embodiment, the delivery catheter, without a stent graft loaded, may be advanced over the guidewire to the treatment site. The stent graft proximal end may be connected to the distal end of the delivery device as previously described. The stent graft may be elongated to reduce the diameter for insertion into the proximal end of introducer tool. The introducer tool may have a distal tapered end to engage the lumen of the delivery catheter and a longitudinal slit for removal. The stent graft may be compressed and advanced into the introducer tool until the proximal end of the stent graft is adjacent the proximal end of the introducer. The insertion tool, stent graft and delivery device distal end can then be placed and advanced over the guidewire until the insertion tool distal end is engaged into the delivery catheter lumen at the proximal end. Advancement of the delivery device moves the stent graft into the bore of the delivery catheter. The stent graft may then be advanced as previously described in order to deploy the stent graft at the treatment site.

In still another alternative procedure for delivering to a target location a stent graft configured in accordance with an exemplary embodiment, a delivery device that replaces the tubular member with an eccentric wire shaft may be utilized. This design for the delivery device, when used for over-the-guidewire delivery, allows the guidewire to run along side the wire shaft (rather than through a tubular shaft as in the above-described procedure). This can allow for the use of shorter rapid exchange length guidewires and facilitate easier device exchange if needed.

Figure 24:
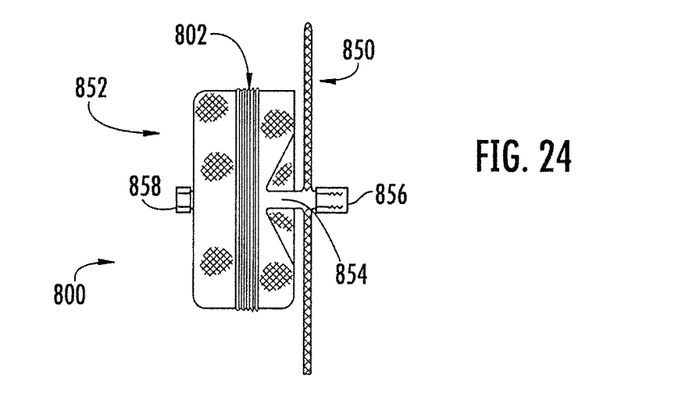
FIG. 24 is a side elevational view of an occlusion device configured in accordance with an exemplary embodiment.

Referring to FIG. 24, therein is shown a side elevational view of an occlusion device 800 utilizing a compressed braid 802 configured in accordance with an exemplary embodiment. The compressed braid 802 is constructed and configured as discussed previously. The device 800 has a disk flange member 850 at one end and a cylindrical member 852 adjacent thereto, connected by an articulation member 854. The compressed braid 802 is positioned on the cylindrical member 852 to provide high radial support for anchoring the device 800 in a vessel. The free ends of the metallic fabric may be secured by clamps 856, 858, as known to those of ordinary skill in the art. For example, the clamp 858 may be configured to engage a delivery device. For example, the delivery device may include a threaded distal end for engagement with a threaded bore formed in the clamp 858 of the occlusion device 800. Further discussion and examples of the procedures by which an occlusion device configured in accordance with exemplary embodiments can be delivered are provided in U.S. patent application Ser. No. 11/966,397 filed Dec. 28, 2007, which is hereby incorporated by reference in its entirety.

Many modifications and other embodiments of the invention set forth herein will come to mind to one skilled in the art to which this invention pertains having the benefit of the teachings presented in the foregoing descriptions and the associated drawings. For example, the side wall need not be entirely cylindrical. Rather, only a portion of the side wall may be cylindrical, with other portions, for example, having irregular or planar surfaces. Further, while some procedures for delivering a medical device configured in accordance with an exemplary embodiment have been described above, other delivery procedures are also possible. For example, certain embodiments are compatible with the graft delivery systems previously disclosed as described in U.S. Pat. Appl. Publ. No. 2007/0118207A1. Considering delivery devices and delivery catheters for medical devices such as occlusion, flow restrictor, and shunt devices, these can generally involve a threaded delivery cable that is threaded to the medical device. The medical device can be collapsed for delivery through the bore of a delivery catheter. The threaded delivery device is used to advance the device through the catheter and artery to the treatment site, at which point the medical device self-expands upon exiting the distal end of the delivery catheter in order to lodge within the vasculature. The delivery device is unthreaded from the device once the proper deployment has been achieved. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for manufacturing a medical device comprising:
   providing a tubular structure comprising at least one layer of metallic material, the tubular structure having a proximal end, a distal end, and a side wall extending therebetween, the tubular structure having an initial diameter in a non-corrugated configuration;

forming the tubular structure such that the side wall defines at least one corrugated surface extending at least partially between the proximal and distal ends, the corrugated surface comprising a plurality of peaks and valleys defining an outer diameter and an inner diameter, respectively, the inner diameter of the valleys being larger than the initial diameter of the tubular structure in the non-corrugated configuration; and heat setting the formed tubular structure in an expanded preset configuration.

2. The method according to claim 1, wherein forming comprises compressing the tubular structure.

3. The method according to claim 2, wherein compressing comprises axially compressing the tubular structure.

4. The method according to claim 1, further comprising braiding the tubular structure from a plurality of metallic strands.

5. The method according to claim 4, wherein forming comprises compressing the tubular structure until the braided plurality of metallic strands repeatedly buckle to define the corrugated surface.

6. The method according to claim 1, wherein providing comprises providing a tubular structure comprising a plurality of layers of metallic material.

7. The method according to claim 1, wherein the tubular structure is configured to be constrained to a reduced configuration and to assume the expanded preset configuration when unconstrained.

8. The method according to claim 1, wherein forming comprises forming a plurality of corrugated portions each comprising a corrugated surface, and wherein at least two corrugated portions of the plurality of corrugated portions are separated from one another by a non-corrugated portion.

9. The method according to claim 1, wherein forming comprises forming the corrugated surface such that each of a plurality of annular ridges extends about an entire circumference of the tubular structure.

10. The method according to claim 1, wherein forming comprises forming the corrugated surface such that each of the plurality of peaks and valleys is offset axially from one another.

11. A method for manufacturing a medical device comprising:

providing a tubular structure having a non-corrugated configuration comprising at least one layer of metallic material, the at least one layer of metallic material comprising a plurality of metallic strands, the tubular structure having a proximal end, a distal end, and a side wall extending therebetween, the tubular structure having an initial inner diameter in the non-corrugated configuration;

compressing the tubular structure such that the side wall defines at least one corrugated surface extending at least partially between the proximal and distal ends, the tubular structure being compressed such that the plurality of metallic strands repeatedly buckle, the at least one corrugated surface having a plurality of peaks and valleys defining an outer diameter and an inner diameter, respectively, the tubular structure being compressed such that an inner diameter of the valleys is larger than the initial diameter of the tubular structure in the non-corrugated configuration; and heat setting the compressed tubular structure.

12. The method according to claim 11, wherein compressing comprises axially compressing the tubular structure.

13. The method according to claim 11, further comprising braiding the tubular structure from the plurality of metallic strands.

14. The method according to claim 11, wherein heat setting comprises heat setting the compressed tubular structure in an expanded preset configuration.

15. The method according to claim 14, wherein the tubular structure is configured to be constrained to a reduced configuration and to assume the expanded preset configuration when unconstrained.

16. The method according to claim 11, wherein compressing comprises compressing the corrugated surface such that each of a plurality of annular ridges extends about an entire circumference of the tubular structure.

17. The method according to claim 11, wherein compressing comprises compressing the tubular structure such that each of the plurality of peaks and valleys is offset axially from one another.

18. The method according to claim 11, wherein compressing comprises compressing the tubular structure without an external mold or an internal mold.

19. The method according to claim 11, wherein compressing comprises compressing the tubular structure such that the plurality of metallic strands have a higher helix angle and a higher density than in the non-corrugated configuration.

20. The method according to claim 11, wherein compressing comprises compressing the tubular structure such that the tubular structure has a greater hoop strength than in the non-corrugated configuration.

* * * * *